US006426424B1

(12) United States Patent
Ashmead et al.

(10) Patent No.: US 6,426,424 B1
(45) Date of Patent: Jul. 30, 2002

(54) COMPOSITION AND METHOD FOR PREPARING GRANULAR AMINO ACID CHELATES AND COMPLEXES

(75) Inventors: Stephen D. Ashmead, Clinton; Mark Pedersen, Kaysville, both of UT (US)

(73) Assignee: Albion International, Inc., Clearfield, UT (US)

( * ) Notice: Subject to any disclaimer, the term of this patent is extended or adjusted under 35 U.S.C. 154(b) by 85 days.

(21) Appl. No.: 09/686,413

(22) Filed: Oct. 11, 2000

(51) Int. Cl.⁷ .............................. C07F 3/00; C07F 15/00; A61K 37/02
(52) U.S. Cl. ............................. 556/1; 556/50; 556/63; 556/116; 556/134; 556/148; 514/6; 514/778; 514/781
(58) Field of Search .................. 556/1, 50, 63, 556/116, 134, 148; 514/6, 778, 781

(56) References Cited

U.S. PATENT DOCUMENTS

| | | | |
|---|---|---|---|
| 2,877,253 A | 3/1959 | Rummel | 260/439 |
| 2,957,806 A | 10/1960 | Rummel | 167/68 |
| 2,960,406 A | 11/1960 | Cardon | 99/2 |
| 3,396,104 A | 8/1968 | Miller | 210/54 |
| 3,463,858 A | 8/1969 | Anderson | 424/289 |
| 3,775,132 A | 11/1973 | Richards, Jr. | 426/364 |
| 4,020,158 A | 4/1977 | Ashmead | 424/177 |
| 4,067,994 A | 1/1978 | Anderson et al. | 424/295 |
| 4,103,003 A | 7/1978 | Ashmead | 424/177 |
| 4,167,564 A | 9/1979 | Jensen | 424/177 |
| 4,169,717 A * | 10/1979 | Ashmead | 71/89 |
| 4,172,072 A | 10/1979 | Ashmead | 260/115 |
| 4,183,947 A | 1/1980 | Cockerill | 424/295 |
| 4,216,143 A | 8/1980 | Ashmead | 260/117 |
| 4,216,144 A | 8/1980 | Ashmead | 260/115 |
| 4,599,152 A | 7/1986 | Ashmead | 204/72 |
| 4,725,427 A | 2/1988 | Ashmead et al. | 424/44 |
| 4,774,089 A | 9/1988 | Ashmead | 424/157 |
| 4,830,716 A | 5/1989 | Ashmead | 204/72 |
| 4,863,898 A | 9/1989 | Ashmead et al. | 514/6 |
| 5,882,685 A * | 3/1999 | Ashmead | 424/617 |
| 5,888,553 A * | 3/1999 | Grant et al. | 424/655 |
| 6,159,530 A * | 12/2000 | Christiansen et al. | 426/656 |
| 6,299,896 B1 * | 10/2001 | Cooper et al. | 424/441 |
| 6,299,914 B1 * | 10/2001 | Christiansen et al. | 426/74 |
| 2002/0009502 A1 * | 1/2002 | Nelson et al. | 424/663 |
| 2002/0025310 A1 * | 2/2002 | Bland | 424/94.1 |

* cited by examiner

Primary Examiner—Porfirio Nazario-Gonzalez
(74) Attorney, Agent, or Firm—Thorpe North & Western, LLP

(57) ABSTRACT

Compositions and methods of preparing amino acid chelates and complexes are disclosed and described. Specifically, by (a) blending hydrated metal sulfate salts, amino acid ligands, and reaction modifiers; (b) confining the particulate blend in an enclosed environment; and (c) applying heat to the particulate blend in the enclosed environment causing the waters of hydration of the metal sulfate salt to be released into the enclosed environment causing a reaction resulting in the formation of a granular amino acid chelate or complex by effecting the reaction between functional electron rich groups of the amino acid ligand and a metal ion of the metal sulfate salt. The waters of hydration serve to provide the water necessary to enable a bonding reaction to take place between the electron rich functional groups of the amino acid ligand and the metal ion of the hydrated metal sulfate salt.

36 Claims, No Drawings

US 6,426,424 B1

COMPOSITION AND METHOD FOR PREPARING GRANULAR AMINO ACID CHELATES AND COMPLEXES

FIELD OF THE INVENTION

The present invention is drawn to compositions and methods of preparing amino acid chelates and complexes. Particularly, by (a) blending a hydrated metal sulfate salt, an amino acid ligand, and a chemically inert reaction modifier; (b) confining the particulate blend in an enclosed environment; and (c) applying heat to the particulate blend in the enclosed environment causing the waters of hydration of the hydrated metal sulfate salt to be released into the enclosed environment such that amino acid chelates and complexes formed are granular and have a desirable particle size and density. The waters of hydration serve to provide the water necessary to enable a bonding reaction to take place between the electron rich functional groups of the amino acid ligand and the metal ion of the hydrated metal sulfate salt.

BACKGROUND OF THE INVENTION

A chelate is a definite structure resulting from precise requirements of synthesis. Proper conditions must be present for chelation to take place including proper mole ratios of ligands to metal ions, pH, and solubility of reactants. As such, traditional "wet" methods of preparing chelates have typically been used to prepare chelates. These methods include the step of dissolving raw materials in solution to ionize the solution or create an appropriate electronic configuration in order for bonding to develop. Though wet methods have typically been used to make chelates, chelates and/or complexes have also been made under dry conditions.

In U.S. Pat. Nos. 2,877,253 and 2,957,806, the entire teachings of which are incorporated by reference, a ferrous sulfate-glycine complex that is substantially free from ferric iron is disclosed. By following the process of dry blending and heating the reactants as is disclosed in these patent applications, at least some complexing and even some chelation occurs. In fact, the above patents teach that there is a distinct color change that takes place as a result of the reaction, i.e. the "complex turns uniformly light brown. However, the reaction is not capable of reacting to completion. This is because a minimum amount of water is needed to drive or catalyze the reaction. Because the reactions described in these patents are carried out in open air conditions, when the waters of hydration are liberated, the liberated water is exposed to the open atmosphere. Thus, some of the liberated water drives the reaction and some is evaporated.

The processes described in U.S. Pat. Nos. 2,877,253 and 2,957,806 have been recently improved as described in two copending U.S. Patent Applications filed of even date herewith entitled "A COMPOSITION AND METHOD FOR PREPARING AMINO ACID CHELATES AND COMPLEXES" and "A COMPOSITION AND METHOD FOR PREPARING AMINO ACID CHELATES AND COMPLEXES FREE OF INTERFERING COMPLEX IONS," both of which are incorporated herein by reference (hereinafter referred to under Attorney Docket Nos. "T8044" and "T8407" respectively). In these applications, the reaction is carried further than the reactions of the above referenced patents (or in many cases carried to completion) because all of the reactants are retained in an enclosed environment. Specifically, by minimizing or eliminating the evaporation of water produced by the hydrated sulfate salt in the reaction blend, the waters of hydration are retained to drive the reaction further than disclosed previously. Though the process described in these two applications produce a chemically desirable product, often the product is an amorphous mass that must be ground and/or dried before the product is acceptable for use in solid dosage forms in the food and pharmaceutical industries.

Chelation can be confirmed and differentiated from mixtures of components by infrared spectrometer analysis (hereinafter "IR"). Essentially, bond stretching and absorption caused by bond formation are analyzed by peak comparison. By utilizing IR, the complexes described in the Rummel patents show a substantial amount of free, unreacted glycine. However, the IR scans also indicate that some chelates and complexes are formed.

As applied in the field of mineral nutrition, there are a few allegedly "chelated" products which are commercially utilized. The first is referred to as a "metal proteinate." The American Association of Feed Control officials (AAFCO) has defined a "metal proteinate" as the product resulting from the chelation of a soluble salt with amino acids and/or partially hydrolyzed proteins. Such products are referred to as the specific metal proteinate, e.g., copper proteinate, zinc proteinate, etc. This definition does not contain any requirements to assure that chelation is actually present. On the basis of the chemical reactant possibilities, there are some real reservations as to the probability of chelation occurring to any great degree. For example, the inclusion of partially hydrolyzed proteins as suitable ligands and the term "and/or" in reference to such ligands implies that products made solely from partially hydrolyzed protein and soluble salts would have the same biochemical and physiological properties as products made from combining amino acids and soluble metal salts. Such an assertion is chemically incorrect. Partially hydrolyzed protein ligands may have molecular weights in the range of thousands of daltons and any bonding between such ligands and a metal ion may be nothing more than a complex or some form of ionic attraction, i.e., the metal drawn in close proximity to carboxyl moiety of such a ligand.

While some products marketed as metal proteinates during the 1960's and 1970's were true chelates, this was prior to the adoption of the AAFCO definition. An analysis of products currently marketed as metal proteinates reveals that most, if not all, are mixtures of metal salts and hydrolyzed protein or complexes between metal salts and hydrolyzed protein. Most are impure products which are difficult to analyze and are not consistent in protein make-up and/or mineral content.

The second product, referred to as an "amino acid chelate," when properly formed, is a stable product having one or more five-membered rings formed by reaction between the carboxyl oxygen, and the $\alpha$-amino group of an $\alpha$-amino acid with the metal ion. Such a five-membered ring is defined by the metal atom, the carboxyl oxygen, the carbonyl carbon, the $\alpha$-carbon and the $\alpha$-amino nitrogen. The actual structure will depend upon the ligand to metal mole ratio. The ligand to metal mole ratio is at least 1:1 and is preferably 2:1 but, in certain instances, may be 3:1 or even 4:1. Most typically, an amino acid chelate may be represented at a ligand to metal ratio of 2:1 according to Formula 1 as follows:

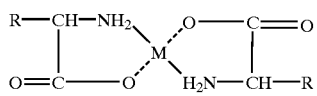

Formula 1

In the above formula, the dashed lines represent coordinate covalent bonds, covalent bonds, or ionic bonds. The solid lines between the α-amino group and the metal (M) are covalent or coordinate covalent bonds. When R is H, the amino acid is glycine which is the simplest of the α-amino acids. However, R could be a radical forming any other of the other twenty or so naturally occurring amino acids derived from proteins. These all have the same configuration for the positioning of the carboxyl oxygen and the α-amino nitrogen. In other words, the chelate ring is defined by the same atoms in each instance.

The American Association of Feed Control Officials (AAFCO) have also issued a definition for an amino acid chelate. It is officially defined as the product resulting from the reaction of a metal ion from a soluble metal salt with amino acids with a mole ratio of one mole of metal to one to three (preferably two) moles of amino acids to form coordinate covalent bonds. The average weight of the hydrolyzed amino acids must be approximately 150 and the resulting molecular weight of the chelate must not exceed 800. The products are identified by the specific metal forming the chelate, e.g., iron amino acid chelate, copper amino acid chelate, etc.

The reason a metal atom can accept bonds over and above the oxidation state of the metal is due to the nature of chelation. In one embodiment of Formula 1, it is noted that one bond is formed from the carboxyl oxygen and the other bond is formed by the α-amino nitrogen which contributes both of the electrons used in the bonding. These electrons fill available spaces in the d-orbitals. This type of bond is known as a dative bond or a coordinate covalent bond and is common in chelation. Thus, a metal ion with a normal valency of +2 can be bonded by four bonds when fully chelated. When chelated in the manner described the divalent metal ion, the chelate is completely satisfied by the bonding electrons and the charge on the metal atom (as well as on the overall molecule) is zero. This neutrality contributes to the bioavailability of metal amino acid chelates.

The structure, chemistry and bioavailability of amino acid chelates is well documented in the literature, e.g. Ashmead et al., Chelated Mineral Nutrition, (1982), Chas. C. Thomas Publishers, Springfield, Ill.; Ashmead et al., Intestinal Absorption of Metal Ions, (1985), Chas. C. Thomas Publishers, Springfield, Ill.; Ashmead et al., Foliar Feeding of Plants with Amino Acid Chelates, (1986), Noyes Publications, Park Ridge, N.J.; U.S. Pat. Nos. 4,020,158; 4,167,564; 4,216,143; 4,216,144; 4,599,152; 4,774,089; 4,830,716; 4,863,898; and 4,725,427, the entire teachings of which are incorporated by reference.

Amino acid chelates can also be formed using peptide ligands instead of single amino acids. These will usually be in the form of dipeptides, tripeptides and sometimes tetrapeptides because larger ligands have a molecular weight which is too great for direct assimilation of the chelate formed. Generally, peptide ligands will be derived by the hydrolysis of protein. However, peptides prepared by conventional synthetic techniques or genetic engineering can also be used. When a ligand is a di- or tripeptide, a radical of the formula $[C(O)CHRNH]_eH$ will replace one of the hydrogens attached to the nitrogen atom in Formula 1. R, as defined in Formula 1, can be H, or the residue of any other naturally occurring amino acid and e can be an integer of 1, 2 or 3. When e is 1 the ligand will be a dipeptide, when e is 2 the ligand will be a tripeptide and so forth.

Based upon what is known about the production of amino acid chelates, it would be useful to provide compositions and methods of preparing amino acid chelates and complexes by improving upon the processes disclosed in U.S. Pat. Nos. 2,877,253 and 2,957,806 and the processes disclosed in T8044 and T8407. Specifically, by preparing chelates and complexes under dry conditions as has been previously disclosed, the preparation process has been simplified and the product produced, often after a grinding step, is stable, granular, dense, dry, and free flowing. However, it would be useful to provide compositions and methods that would enable the production of an even more granular, dense, and free flowing product. Additionally, it would be useful to provide compositions and methods that minimize the formation of amorphous masses of product, thereby drastically reducing or eliminating the need for a grinding step.

SUMMARY OF THE INVENTION

The present invention is drawn to compositions and methods wherein particulate amino acids are blended with particulate hydrated metal sulfate salts and reaction modifiers. The blend is then placed in an enclosed (preferably virtually sealed) environment and heated under low to moderate temperatures for a time sufficient that the waters of hydration from the hydrated metal sulfate salt are released and provide the moisture necessary to effect a bonding reaction between the electron rich functional groups of the amino acid ligand with the metal ion of the sulfate salt, thereby forming amino acid chelates and complexes that are more granular, dense, and free flowing than other amino acid chelates prepared under similar reaction conditions.

DETAILED DESCRIPTION OF THE INVENTION

Before the present invention pertaining to the preparation of amino acid chelates and complexes is disclosed and described, it is to be understood that this invention is not limited to the particular process steps and materials disclosed herein because such process steps and materials may vary somewhat. It is also to be understood that the terminology used herein is used for the purpose of describing particular embodiments only. The terms are not intended to be limiting because the scope of the present invention is intended to be limited only by the appended claims and equivalents thereof.

It must also be noted that, as used in this specification and the appended claims, the singular forms "a," "37 an," and "the" include plural referents unless the content clearly dictates otherwise.

The terms "metal" and "mineral" may be used interchangeably.

"Hydrated metal sulfate salt," "metal sulfate hydrate," or "metal sulfate salt having waters of hydration" includes any metal sulfate salt that has one or more waters of hydration capable of being released in the reactions of the present invention.

"Hydrate" is meant to include any degree of hydration attached to the metal sulfate salts, e.g., monohydrate, dihydrate, trihydrate, tetrahydrate, pentahydrate, hexahydrate, septahydrate, octahydrate, nonahydrate, etc.

"Nutritionally relevant metals" include metals that are known to be needed by living organisms, particularly plants and mammals, including humans. Metals such as Cu, Zn, Fe, Co, Mg, Mn, Cr, Mo, among others are exemplary of nutritionally relevant metals.

"Amino acid chelates" or "amino acid chelates and complexes" are meant to include metal ions bonded to amino acid ligands forming heterocyclic rings. The bonds may be coordinate covalent, covalent, and/or ionic at the carboxyl oxygen group. However, at the α-amino group, the bond is typically a coordinate covalent bond.

"Enclosed chamber" or "enclosed environment" shall include any system or container that is capable of being substantially sealed or closed such that the waters of hydration released from a hydrate are substantially retained, thereby providing water to drive any reaction within the system or container.

"Reaction modifier" or "inert reaction modifier" includes any modifier that may be added to the core reactants, i.e., the amino acid ligand and the hydrated sulfate salt, to improve the physical properties of the product. Preferred reaction modifiers include starches, partially hydrolyzed starches, celluloses, partially hydrolyzed celluloses, and combinations thereof. Examples of sources for the reaction modifier include rice flour, corn starch, potato starch, microcrystalline cellulose, powdered cellulose, maltodextrin, and modified food starch.

With this in mind, compositions and methods of preparing amino acid chelates and complexes by blending and heating an amino acid ligand with a hydrated metal sulfate salt in an enclosed environment is disclosed and described. A method of preparing amino acid chelates and complexes comprises the steps of (a) combining a metal sulfate salt having waters of hydration, an amino acid ligand, and a reaction modifier to form a particulate blend, wherein the ligand to metal molar ratio is from about 1:1 to 4:1; (b) confining the particulate blend in an enclosed environment; and (c) applying heat to the particulate blend in the enclosed environment causing the waters of hydration of the hydrated metal sulfate salt to be released into the enclosed environment such that the amino acid chelates and complexes formed are granular and have a desirable particle size and density. The waters of hydration serve to provide the water necessary to enable a bonding reaction to take place between the electron rich functional groups of the amino acid ligand and the metal ion of the hydrated metal sulfate salt. The particulate blend should be allowed to react for a sufficient amount of time to drive the waters of hydration from the hydrated sulfate salt into the enclosed environment, thereby causing the formation of an amino acid chelate or complex by effecting the reaction between functional electron rich groups of the ligands and the metal ion of the metal sulfate salt. This process results in particulate amino acid chelates and complexes that are more stable, granular, dense, dry, and/or free flowing than those described in the prior art.

Though acceptable amino acid chelates may be formed without the addition of reaction modifiers, such as those described in T8044 and T8407, the addition of reaction modifiers improve the physical properties of the product. Among the physical properties that are improved by the present invention include increased particle size, more uniform particle size, increased product density, and increased compressibility in the manufacture of solid dosage forms. Additionally, the formation of amorphous masses of product is minimized, thereby drastically reducing or eliminating the need for a grinding step.

The reaction modifiers that enhance the physical properties of the compositions and methods of the present invention include any combination of starches, partially hydrolyzed starches, powdered cellulose, and/or modified cellulose. These modifiers may be provided from any know source or in any known form. The amount of any one or combination of the above reaction modifiers required to enhance the physical properties of the product can range from 1–30% of the weight of the product. However, preferred ranges are from about 15–25%.

If a combination of reaction modifiers are used, the preferred combination should include a source of starch. The starch acts to gelatinize and absorb any excess water released from the reaction of the hydrated soluble sulfate salt(s) and the amino acid(s). The absorptive qualities of the reaction modifier aids in the granulation effect of the process. In addition, the material produced by this process is easier to handle because the product flows from the reaction vessel more continuously rather than forming an amorphous mass that must be mechanically ground (often after drying) to a suitable particle size before packaging. The addition of the reaction modifiers to the process results in a product that has a particle size range of about 16–80 mesh, with only a few oversized particles. This is significant because the desired particle size range for the majority of solid dosage forms in the food and pharmaceutical industries fall within this range. Additionally, the density of the product produced by the present invention increases from about 0.5–0.7 gm/cc (via methods disclosed in T8044 and T8407) to about 0.75–0.95 gm/cc (via methods disclosed in the present invention).

Though the preferred embodiment of the invention does not include the addition of water, some additional water may be added to effectuate desired results, e.g., copper sulfate monohydrate may not have enough waters of hydration to progress a reaction to substantial completion. Therefore, water may optionally be added in very small amounts to assist specific reactions. If water is added, the water should preferably not be added such that there is a substantial excess after the reaction has progressed to substantial completion. For example, if zinc monohydrate was used as a reactant instead of zinc pentahydrate in a formulation where zinc pentahydrate would likely drive the reaction closer to completion, 4 molar equivalents of water could be added to the blend prior to enclosing the reactants to simulate the effect of adding zinc pentahydrate. In most circumstances and in accordance with this aspect of the present invention, from about 1 to 15 molar equivalents of water can be added.

The step of enclosing the particulate blend is important because the waters of hydration must not be allowed to substantially evaporate during the reaction. This is because the waters of hydration are necessary to drive the reaction between the ligand and the metal ion of the hydrated metal sulfate salt. Therefore, a virtually sealed environment is preferred, though an enclosure that prevents substantial contact between the reaction blend and the atmosphere will also provide desired results.

Generally, time and temperature variables should be considered when determining whether the reaction has been driven to a desired product. A typical temperature range is from about 60° C. to 90° C., though temperatures outside of this range may be used. In a preferred embodiment, the particulate blend in the enclosed chamber may be heated to about 70° C. for about 90 minutes. After, heating the particulate blend, the resulting product is allowed to cool to room temperature. The product is then exposed to the atmosphere and allowed to stand overnight. However, the heating time and temperature as well as the cooling time and temperature will depend largely upon what metal salts, ligands, ratios, batch sizes, etc., are selected.

In order for the reaction to be driven forward, the hydrated metal sulfate salt must have at least one water molecule available for release to catalyze the reaction. However, if for example, a metal sulfate monohydrate is used, the reaction will not advance as far as other, more hydrated, metal salts. Conversely, hydrated metal sulfate salts such as a metal sulfate pentahydrate or heptahydrate (or even higher) are preferred compounds because of the number of water molecules available for liberation during the reaction. For example, ferrous sulfate heptahydrate is one of many ideal salts to utilize as will be exemplified below.

Since the ligands of the present invention are generally amino acids, the naturally occurring amino acids including alanine, arginine, asparagine, aspartic acid, cysteine, cystine, glutamine, glutamic acid, glycine, histidine, hydroxyproline, isoleucine, leucine, lysine, methionine, ornithine, phenylalanine, proline, serine, threonine, tryptophan, tyrosine, valine, and combinations thereof are preferred. However, ligands including dipeptides, tripeptides, and tetrapeptides formed by any combination of the aforementioned amino acids may be used.

If the ligand and/or hydrated metal sulfate salts are in something other than powder form, e.g. larger crystals, etc., an additional step of grinding the raw materials into powder is preferred. As such, large hydrated metal sulfate salts and ligands should be ground in to a maximum particle size of 80 mesh, preferably from 20 to 80 mesh. Further, the enclosed chamber previously discussed may be a device as simple as a calorimeter, a plastic lined container, or a plastic bag capable of being enclosed or sealed. However, other enclosed chambers and systems are within the scope of the invention.

There are two major advantages to producing amino acid chelates and complexes as described above. First, as mentioned previously, the waters of hydration are maintained within the closed system and are used to drive the reaction forward to a greater degree than the prior art has taught. However, the enclosed chamber serves a second and important function. Granules are allowed to form under these conditions, though the addition of the reaction modifiers of the present invention increase granulation. After sufficient reaction time, the color of the particulate blend completely changes in color and texture. Hydrated granules form that are free-flowing and generally range in size from 20 to 80 mesh. However, due to the presence of the reaction modifiers, clumping of the granules is minimized. Further, while cooling, the reaction continues to progress slowly until a dry granule product forms that is stable, dense, and free flowing. The reaction time may be very short or may require multiple days, depending on the embodiment.

Amino acid chelates and complexes of the present invention have many possible applications. First, they may be used as plant foliars and foods. Either the product could be dissolved for use on leaves, etc., or used directly as a soil treatment. Further, the product could be dry blended in combination with other metal salts and a variety of ligands for more unique applications. These chelates and complexes could also be used in animal feeds by methods currently known in the art. Additionally, some processes may create products that could be used in food applications for warm-blooded animals, including humans.

EXAMPLES

The following examples illustrate compositions and methods of preparing the amino acid chelates and complexes of the present invention. The following examples should not be considered as limitations of the present invention, but should merely teach how to make the best known amino acid chelates and complexes based upon current experimental data.

Example 1

One mole of ferrous sulfate heptahydrate powder, two moles of glycine powder, and 20% by weight of rice flour (90% starch content) were dry blended and placed in a bomb calorimeter. The calorimeter was submersed in a water bath maintained at about 70° C. for about 90 minutes. The calorimeter was removed from the water bath and allowed to cool to room temperature. The calorimeter was then opened and the product was allowed to stand overnight. A ferrous glycine chelate complex was formed having ligand to metal molar ratio of about 2:1 and an iron content of about 11% by weight. The particle size of the product was then analyzed on a Ro-Tap screen shaker fitted with 16, 20, 40, 60, 80, and 100 mesh screens. About 19% of the product did not pass through a 20 mesh screen, 58% of the product was between 20–60 mesh, and 23% of the product passed through a 60 mesh screen. The bulk density of a 20–80 mesh cut of the product measured about 0.92 gm/cc.

Example 2

One mole of copper sulfate pentahydrate powder, two moles of L-lysine powder, 10% by weight of corn starch (90% starch content), and 10% rice flour (90% starch content) were dry blended and placed in a bomb calorimeter. The calorimeter was submersed in a water bath maintained at about 70° C. for about 90 minutes. The calorimeter was removed from the water bath and allowed to cool to room temperature. The calorimeter was then opened and the product was allowed to stand overnight. A copper lysine chelate complex was formed having ligand to metal molar ratio of about 2:1 and a copper content of about 9.5% by weight. The particle size of the product was then analyzed on a Ro-Tap screen shaker fitted with 16, 20, 40, 60, 80, and 100 mesh screens. About 16% of the product did not pass through a 20 mesh screen, 49% of the product was between 20–60 mesh, and 35% of the product passed through a 60 mesh screen. The bulk density of a 20–80 mesh cut of the product measured about 0.95 gm/cc.

Example 3

One mole of zinc sulfate heptahydrate powder, on mole of manganese sulfate pentahydrate powder, four moles of glycine powder, 10% by weight of corn starch (90% starch content), and 10% by weight of microcrystalline cellulose were dry blended and placed in a bomb calorimeter. The calorimeter was submersed in a water bath maintained at about 70° C. for about 90 minutes. The calorimeter was removed from the water bath and allowed to cool to room temperature. The calorimeter was then opened and the product was allowed to stand overnight. A zinc glycine chelate complex was formed having ligand to metal molar ratio of about 2:1 and a zinc content of about 6.3% by weight. A manganese glycine chelate complex was also formed having ligand to metal molar ratio of about 2:1 and a manganese content of about 5.3% by weight. The particle size of the product was then analyzed on a Ro-Tap screen shaker fitted with 16, 20, 40, 60, 80, and 100 mesh screens. About 25% of the product did not pass through a 20 mesh screen, 56% of the product was between 20–60 mesh, and 19% of the product passed through a 60 mesh screen. The bulk density of a 20–80 mesh cut of the product measured about 0.87 gm/cc.

Example 4

One mole of magnesium sulfate nonahydrate powder, one mole of glycine powder, one mole of L-methionine powder, 10% by weight of potato starch, and 10% powdered cellulose were dry blended and placed in a bomb calorimeter. The calorimeter was submersed in a water bath maintained at about 70° C. for about 90 minutes. The calorimeter was removed from the water bath and allowed to cool to room temperature. The calorimeter was then opened and the product was allowed to stand overnight. Various combinations of magnesium amino acid chelate complexes, i.e., glycine and methionine ligands, were formed having ligand to metal molar ratio of about 2:1 and an magnesium content of about 4.5% by weight. The particle size of the product was then analyzed on a Ro-Tap screen shaker fitted with 16, 20, 40, 60, 80, and 100 mesh screens. About 22% of the product did not pass through a 20 mesh screen, 51% of the product was between 20–60 mesh, and 27% of the product passed through a 60 mesh screen. The bulk density of a 20–80 mesh cut of the product measured about 0.81 gm/cc.

Example 5

One mole of zinc sulfate heptahydrate powder, one mole of manganese sulfate pentahydrate powder, one mole of copper sulfate pentahydrate powder, two moles of glycine powder, two moles of L-lysine base powder, and two moles of L-histidine powder, 10% by weight of maltodextrin, 10% by weight corn starch, and 5% by weight of microcrystalline cellulose were dry blended and placed in a bomb calorimeter. The calorimeter was submersed in a water bath maintained at about 70° C. for about 90 minutes. The calorimeter was removed from the water bath and allowed to cool to room temperature. The calorimeter was then opened and the product was allowed to stand overnight. Zinc amino acid chelates, manganese amino acid chelates, and copper amino acid chelates having a ligand to metal molar ratio of about 2:1 were produced having ligand combinations of glycine, lysine, and histidine. The zinc content was about 3.3% by weight, the manganese content was about 2.8% by weight, and the copper content was about 3.2% by weight. The particle size of the product was then analyzed on a Ro-Tap screen shaker fitted with 16, 20, 40, 60, 80, and 100 mesh screens. About 15% of the product did not pass through a 20 mesh screen, 62% of the product was between 20–60 mesh, and 23% of the product passed through a 60 mesh screen. The bulk density of a 20–80 mesh cut of the product measured about 0.90 gm/cc.

Example 6

One mole of copper sulfate pentahydrate, one mole of glycine, 10% by weight maltodextrin, 10% by weight rice flour (90% starch content) were dry blended and placed in a bomb calorimeter. The calorimeter was immersed in a water bath maintained ate about 70° C. for about 90 minutes. The calorimeter was removed from the water bath and allowed to cool to room temperature. The calorimeter was then opened and the product was allowed to stand overnight. A granular copper glycine chelate complex was formed having a ligand to metal molar ratio of about 1:1 and a copper content of about 16% by weight.

Example 7

One mole of ferric sulfate hydrate (about 20% water), two moles of glycine, one mole of lysine, 10% by weight potato starch, and 10% by weight microcrystalline cellulose were dry blended and placed in a bomb calorimeter. The calorimeter was immersed in a water bath maintained ate about 70° C. for about 90 minutes. The calorimeter was removed from the water bath and allowed to cool to room temperature. The calorimeter was then opened and the product was allowed to stand overnight. A granular ferric amino acid chelate complex was formed having a ligand to metal molar ratio of about 3:1 and ligand combination s of glycine and lysine. The iron content was about 12% by weight.

While the invention has been described with reference to certain preferred embodiments, those skilled in the art will appreciate that various modifications, changes, omissions, and substitutions can be made without departing from the spirit of the invention. It is intended, therefore, that the invention be limited only by the scope of the following claims.

We claim:

1. A method of preparing amino acid chelates and complexes comprising the steps of:
    a) combining as a particulate blend
        i) a hydrated metal sulfate salt having one or more waters of hydration,
        ii) an amino acid ligand, and
        iii) a reaction modifier wherein the ligand to metal molar ratio is from about 1:1 to 4:1;
    b) confining the particulate blend in an enclosed environment; and
    c) applying heat to the particulate blend in the enclosed environment causing the waters of hydration of the metal sulfate salt to be released into the enclosed environment causing a reaction resulting in the formation of a granular amino acid chelate or complex by effecting the reaction between functional electron rich groups of the amino acid ligand and a metal ion of the metal sulfate salt.

2. A method as in claim 1 wherein said metal sulfate salt is selected from the group consisting of iron sulfate hydrates, copper sulfate hydrates, zinc sulfate hydrates, manganese sulfate hydrates, cobalt sulfate hydrates, magnesium sulfate hydrates, chromium sulfate hydrates, molybdenum sulfate hydrates, and combinations thereof.

3. A method as in claim 1 wherein said amino acid ligand is selected from the group consisting of alanine, arginine, asparagine, aspartic acid, cysteine, cystine, glutamine, glutamic acid, glycine, histidine, hydroxyproline, isoleucine, leucine, lysine, methionine, ornithine, phenylalanine, proline, serine, threonine, tryptophan, tyrosine, valine, and combinations thereof, and dipeptides, tripeptides, and tetrapeptides formed by any combination of the amino acids thereof.

4. A method as in claim 1 wherein the reaction modifier is selected from the group consisting of starches, partially hydrolyzed starches, celluloses, partially hydrolyzed celluloses, and combinations thereof.

5. A method as in claim 2 wherein the hydrated metal sulfate salt is selected from the group consisting of ferrous sulfate tetrahydrate, ferrous sulfate heptahydrate, copper sulfate pentahydrate, manganese sulfate pentahydrate, zinc sulfate heptahydrate, magnesium sulfate nonahydrate, chromium sulfate heptahydrate, cobalt sulfate heptahydrate, molybdenum sulfate hydrate, and combinations thereof.

6. A method as in claim 3 wherein the amino acid ligand is glycine.

7. A method as in claim 3 wherein the amino acid ligand is lysine.

8. A method as in claim 3 wherein the amino acid ligand is methionine.

9. A method as in claim 3 wherein the amino acid ligand is comprised of glycine and one of the other naturally occurring amino acids.

10. A method as in claim 4 wherein the reaction modifier is selected from the group consisting of rice flour, corn starch, potato starch, microcrystalline cellulose, powdered cellulose, maltodextrin, modified food starches, and combinations thereof.

11. A method as in claim 1 wherein the reaction modifier is present at from about 1–30% by weight.

12. A method as in claim 11 wherein the reaction modifier is present at from about 15–25% by weight.

13. A method as in claim 1 wherein the particulate blend in the enclosed environment is heated at temperatures from 60° C. to 90° C.

14. A method as in claim 13 wherein the particulate blend in the enclosed environment is heated at about 70° C.

15. A method as in claim 13 wherein, following the heating step, the temperature of the particulate blend is reduced to room temperature and allowed to continue to react.

16. A method as in claim 1 having a preliminary step of grinding the ligand and the hydrated metal sulfate salt into powder from about 20 to 80 mesh.

17. A method as in claim 1 wherein the enclosed environment is selected from the group consisting of a calorimeter, a plastic lined container, a plastic bag, and combinations thereof.

18. A method as in claim 1 wherein a minor amount of water is added to the particulate blend to drive the reaction toward completion.

19. Particulate amino acid chelates and complexes prepared by the process of:
   a) combining as a particulate blend
      i) a hydrated metal sulfate salt having one or more waters of hydration,
      ii) an amino acid ligand, and
      iii) a reaction modifier wherein the ligand to metal molar ratio is from about 1:1 to 4:1;
   b) confining the particulate blend in an enclosed environment; and
   c) applying heat to the particulate blend in the enclosed environment causing the waters of hydration of the metal sulfate salt to be released into the enclosed environment causing a reaction resulting in the formation of a granular amino acid chelate or complex by effecting the reaction between functional electron rich groups of the amino acid ligand and a metal ion of the metal sulfate salt.

20. Particulate amino acid chelates and complexes of claim 19 wherein said metal sulfate salt is selected from the group consisting of iron sulfate hydrates, copper sulfate hydrates, zinc sulfate hydrates, manganese sulfate hydrates, cobalt sulfate hydrates, magnesium sulfate hydrates, chromium sulfate hydrates, molybdenum sulfate hydrates, and combinations thereof.

21. Particulate amino acid chelates and complexes as in claim 19 wherein said amino acid ligand is selected from the group consisting of alanine, arginine, asparagine, aspartic acid, cysteine, cystine, glutamine, glutamic acid, glycine, histidine, hydroxyproline, isoleucine, leucine, lysine, methionine, ornithine, phenylalanine, proline, serine, threonine, tryptophan, tyrosine, valine, and combinations thereof, and dipeptides, tripeptides, and tetrapeptides formed by any combination of the amino acids thereof.

22. Particulate amino acid chelates and complexes as in claim 19 wherein the reaction modifier is selected from the group consisting of starches, partially hydrolyzed starches, celluloses, partially hydrolyzed celluloses, and combinations thereof.

23. Particulate amino acid chelates and complexes as in claim 20 wherein the hydrated metal sulfate salt is selected from the group consisting of ferrous sulfate tetrahydrate, ferrous sulfate heptahydrate, copper sulfate pentahydrate, manganese sulfate pentahydrate, zinc sulfate heptahydrate, magnesium sulfate nonahydrate, chromium sulfate heptahydrate, cobalt sulfate heptahydrate, molybdenum sulfate hydrate, and combinations thereof.

24. Particulate amino acid chelates and complexes as in claim 21 wherein the amino acid ligand is glycine.

25. Particulate amino acid chelates and complexes as in claim 21 wherein the amino acid ligand is lysine.

26. Particulate amino acid chelates and complexes as in claim 21 wherein the amino acid ligand is methionine.

27. Particulate amino acid chelates and complexes as in claim 21 wherein the amino acid ligand is comprised of glycine and one of the other naturally occurring amino acids.

28. Particulate amino acid chelates and complexes as in claim 20 wherein the reaction modifier is selected from the group consisting of rice flour, corn starch, potato starch, microcrystalline cellulose, powdered cellulose, maltodextrin, modified food starch, and combinations thereof.

29. Particulate amino acid chelates and complexes as in claim 19 wherein the reaction modifier is present at from about 1–30% by weight.

30. Particulate amino acid chelates and complexes as in claim 29 wherein the reaction modifier is present at from about 15–25% by weight.

31. Particulate amino acid chelates and complexes as in claim 19 wherein the particulate blend in the enclosed environment is heated at temperatures from 60° C. to 90° C.

32. Particulate amino acid chelates and complexes as in claim 31 wherein the particulate blend in the enclosed environment is heated at about 70° C.

33. Particulate amino acid chelates and complexes as in claim 31 wherein, following the heating step, the temperature of the particulate blend is reduced to room temperature and allowed to continue to react.

34. Particulate amino acid chelates and complexes as in claim 19 having a preliminary step of grinding the ligand and the hydrated metal sulfate salt into powder from about 20 to 80 mesh.

35. Particulate amino acid chelates and complexes as in claim 19 wherein the enclosed environment is selected from the group consisting of a calorimeter, a plastic lined container, a plastic bag, and combinations thereof.

36. Particulate amino acid chelates and complexes as in claim 19 wherein a minor amount of water is added to the particulate blend to drive the reaction.

* * * * *